United States Patent
Trees et al.

(10) Patent No.: US 9,848,937 B2
(45) Date of Patent: Dec. 26, 2017

(54) END EFFECTOR WITH DETECTABLE CONFIGURATIONS

(71) Applicant: Ethicon Endo-Surgery, Inc., Cincinnati, OH (US)

(72) Inventors: Gregory A. Trees, Loveland, OH (US); Geoffrey S. Strobl, Williamsburg, OH (US)

(73) Assignee: Ethicon LLC, Guaynabo, PR (US)

( * ) Notice: Subject to any disclaimer, the term of this patent is extended or adjusted under 35 U.S.C. 154(b) by 421 days.

(21) Appl. No.: 14/579,230

(22) Filed: Dec. 22, 2014

(65) Prior Publication Data

US 2016/0175028 A1   Jun. 23, 2016

(51) Int. Cl.
*A61B 18/14* (2006.01)
*A61B 18/00* (2006.01)
*A61B 90/00* (2016.01)

(52) U.S. Cl.
CPC ...... *A61B 18/1445* (2013.01); *A61B 2018/00071* (2013.01); *A61B 2018/00702* (2013.01); *A61B 2018/00791* (2013.01); *A61B 2018/00815* (2013.01); *A61B 2018/00875* (2013.01); *A61B 2090/034* (2016.02)

(58) Field of Classification Search
CPC ............ A61B 18/1442; A61B 18/1445; A61B 2018/00071; A61B 2018/00077; A61B 2018/00875; A61B 2018/00642; A61B 2018/00702; A61B 2018/00666
USPC ................................. 606/41, 50–52
See application file for complete search history.

(56) References Cited

U.S. PATENT DOCUMENTS

| | | | |
|---|---|---|---|
| 2,366,274 A | 1/1945 | Luth et al. |
| 2,458,152 A | 1/1949 | Eakins |
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |

(Continued)

FOREIGN PATENT DOCUMENTS

| | | |
|---|---|---|
| CN | 2868227 Y | 2/2007 |
| DE | 4300307 A1 | 7/1994 |

(Continued)

OTHER PUBLICATIONS

U.S. Appl. No. 14/229,033, filed Mar. 28, 2014.

(Continued)

*Primary Examiner* — Thomas Giuliani

(57) ABSTRACT

A surgical end effector has a first jaw comprising a first electrode and a second jaw, wherein at least one of the first jaw and the second jaw is movable relative to the other one of the first jaw and the second jaw to transition the end effector between an open configuration, an approximated configuration, and a fully approximated configuration. The second jaw includes a second electrode and a spacer extending from the second electrode, wherein the spacer is configured to maintain a predetermined distance between the first electrode and the second electrode when the end effector is in the fully approximated configuration, wherein the spacer is in contact with the first electrode in the fully approximated configuration, wherein the spacer is spaced apart from the first electrode in the open configuration, and wherein the spacer is comprised of a semi-conductive material.

11 Claims, 13 Drawing Sheets

(56) References Cited

U.S. PATENT DOCUMENTS

| | | |
|---|---|---|
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,836,909 A | 11/1998 | Cosmescu |
| 5,836,943 A | 11/1998 | Miller, III |
| 5,836,990 A | 11/1998 | Li |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |

(56) References Cited

U.S. PATENT DOCUMENTS

| | | |
|---|---|---|
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| 6,132,368 A | 10/2000 | Cooper |
| 6,144,402 A | 11/2000 | Norsworthy et al. |
| 6,152,923 A | 11/2000 | Ryan |
| 6,154,198 A | 11/2000 | Rosenberg |
| 6,162,208 A | 12/2000 | Hipps |
| 6,174,309 B1 | 1/2001 | Wrublewski et al. |
| 6,176,857 B1 | 1/2001 | Ashley |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,109 B1 | 5/2002 | Davison et al. |
| 6,391,026 B1 | 5/2002 | Hung et al. |
| 6,398,779 B1 | 6/2002 | Buysse et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,689 B1 | 10/2002 | Qin et al. |
| 6,464,702 B2 | 10/2002 | Schulze et al. |
| 6,480,796 B2 | 11/2002 | Wiener |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,551,309 B1 | 4/2003 | LePivert |
| 6,554,829 B2 | 4/2003 | Schulze et al. |
| 6,558,376 B2 | 5/2003 | Bishop |
| 6,562,037 B2 | 5/2003 | Paton et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,644,532 B2 | 11/2003 | Green et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,673,248 B2 | 1/2004 | Chowdhury |
| 6,679,882 B1 | 1/2004 | Kornerup |
| 6,695,840 B2 | 2/2004 | Schulze |
| 6,719,765 B2 | 4/2004 | Bonutti |
| 6,722,552 B2 | 4/2004 | Fenton, Jr. |
| 6,733,498 B2 | 5/2004 | Paton et al. |
| 6,746,443 B1 | 6/2004 | Morley et al. |
| 6,752,815 B2 | 6/2004 | Beaupre |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrodinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,977,495 B2 | 12/2005 | Donofrio |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |

(56) References Cited

U.S. PATENT DOCUMENTS

| | | |
|---|---|---|
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,980,443 B2 | 7/2011 | Scheib et al. |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,048,070 B2 | 11/2011 | O'Brien et al. |
| 8,056,720 B2 | 11/2011 | Hawkes |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,075,555 B2 | 12/2011 | Truckai et al. |
| 8,075,558 B2 | 12/2011 | Truckai et al. |
| 8,100,894 B2 | 1/2012 | Mucko et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,186,560 B2 | 5/2012 | Hess et al. |
| 8,187,267 B2 | 5/2012 | Pappone et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,277,471 B2 | 10/2012 | Wiener et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,232 B2 | 10/2012 | Unger |
| 8,303,583 B2 | 11/2012 | Hosier et al. |
| 8,308,040 B2 | 11/2012 | Huang et al. |
| 8,323,310 B2 | 12/2012 | Kingsley |
| 8,328,761 B2 | 12/2012 | Widenhouse et al. |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |

(56) References Cited

U.S. PATENT DOCUMENTS

| | | |
|---|---|---|
| 8,338,726 B2 | 12/2012 | Palmer et al. |
| 8,357,158 B2 | 1/2013 | McKenna et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,491,625 B2 | 7/2013 | Horner |
| 8,496,682 B2 | 7/2013 | Guerra et al. |
| 8,512,364 B2 | 8/2013 | Kowalski et al. |
| 8,529,437 B2 | 9/2013 | Taylor et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,579,176 B2 | 11/2013 | Smith et al. |
| 8,591,506 B2 | 11/2013 | Wham et al. |
| D695,407 S | 12/2013 | Price et al. |
| 8,613,383 B2 | 12/2013 | Beckman et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,640,788 B2 | 2/2014 | Dachs, II et al. |
| 8,647,350 B2 | 2/2014 | Mohan et al. |
| 8,652,120 B2 | 2/2014 | Giordano et al. |
| 8,663,220 B2 | 3/2014 | Wiener et al. |
| 8,663,222 B2 | 3/2014 | Anderson et al. |
| 8,668,691 B2 | 3/2014 | Heard |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,708,213 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,770,459 B2 | 7/2014 | Racenet et al. |
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,814,856 B2 | 8/2014 | Elmouelhi et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,851,354 B2 | 10/2014 | Swensgard et al. |
| 8,864,757 B2 | 10/2014 | Klimovitch et al. |
| 8,864,761 B2 | 10/2014 | Johnson et al. |
| 8,882,766 B2 | 11/2014 | Couture et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,961,515 B2 | 2/2015 | Twomey et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,028,494 B2 | 5/2015 | Shelton, IV et al. |
| 9,028,519 B2 | 5/2015 | Yates et al. |
| 9,039,695 B2 | 5/2015 | Giordano et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,050,093 B2 | 6/2015 | Aldridge et al. |
| 9,050,098 B2 | 6/2015 | Deville et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,101,385 B2 | 8/2015 | Shelton, IV et al. |
| 9,113,900 B2 | 8/2015 | Buysse et al. |
| 9,119,657 B2 | 9/2015 | Shelton, IV et al. |
| 9,125,662 B2 | 9/2015 | Shelton, IV |
| 9,125,667 B2 | 9/2015 | Stone et al. |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,216,050 B2 | 12/2015 | Condie et al. |
| 9,220,559 B2 | 12/2015 | Worrell et al. |
| 9,226,751 B2 | 1/2016 | Shelton, IV et al. |

(56) References Cited

U.S. PATENT DOCUMENTS

| | | |
|---|---|---|
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,333,025 B2 | 5/2016 | Monson et al. |
| 9,339,323 B2 | 5/2016 | Eder et al. |
| 9,345,900 B2 | 5/2016 | Wu et al. |
| 9,351,754 B2 | 5/2016 | Vakharia et al. |
| 9,364,230 B2 | 6/2016 | Shelton, IV et al. |
| 9,375,232 B2 | 6/2016 | Hunt et al. |
| 9,375,267 B2 | 6/2016 | Kerr et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,526,564 B2 | 12/2016 | Rusin |
| 9,526,565 B2 | 12/2016 | Strobl |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 2002/0022836 A1 | 2/2002 | Goble et al. |
| 2002/0049551 A1 | 4/2002 | Friedman et al. |
| 2002/0107517 A1 | 8/2002 | Witt et al. |
| 2003/0014053 A1 | 1/2003 | Nguyen et al. |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0199869 A1* | 10/2003 | Johnson ............ A61B 18/1445 606/50 |
| 2003/0229344 A1 | 12/2003 | Dycus et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0090817 A1 | 4/2005 | Phan |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0256405 A1 | 11/2005 | Makin et al. |
| 2005/0267464 A1 | 12/2005 | Truckai et al. |
| 2006/0058825 A1 | 3/2006 | Ogura et al. |
| 2006/0064086 A1 | 3/2006 | Odom |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0188755 A1 | 8/2008 | Hart |
| 2008/0214967 A1 | 9/2008 | Aranyi et al. |
| 2008/0281315 A1 | 11/2008 | Gines |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082766 A1 | 3/2009 | Unger et al. |
| 2009/0112229 A1 | 4/2009 | Omori et al. |
| 2009/0131929 A1 | 5/2009 | Shimizu |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0240246 A1* | 9/2009 | Deville ............ A61B 18/1445 606/33 |
| 2009/0248002 A1 | 10/2009 | Takashino et al. |
| 2009/0248021 A1 | 10/2009 | McKenna |
| 2009/0254080 A1 | 10/2009 | Honda |
| 2009/0287205 A1 | 11/2009 | Ingle |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0222752 A1 | 9/2010 | Collins, Jr. et al. |
| 2010/0274278 A1 | 10/2010 | Fleenor et al. |
| 2011/0087220 A1 | 4/2011 | Felder et al. |
| 2011/0276049 A1 | 11/2011 | Gerhardt |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0083784 A1* | 4/2012 | Davison ............ A61B 18/1445 606/48 |
| 2012/0109186 A1 | 5/2012 | Parrott et al. |
| 2012/0116265 A1 | 5/2012 | Houser et al. |
| 2012/0116391 A1 | 5/2012 | Houser et al. |
| 2012/0143182 A1* | 6/2012 | Ullrich ............... A61B 18/1445 606/45 |
| 2012/0173943 A1* | 7/2012 | Cesari ............ G01B 31/318552 714/731 |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0085496 A1 | 4/2013 | Unger et al. |
| 2013/0123776 A1 | 5/2013 | Monson et al. |

(56) References Cited

U.S. PATENT DOCUMENTS

| | | |
|---|---|---|
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005681 A1 | 1/2014 | Gee et al. |
| 2014/0005694 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094795 A1* | 4/2014 | Keller ............... A61B 18/085 606/34 |
| 2014/0194874 A1 | 7/2014 | Dietz et al. |
| 2014/0194875 A1 | 7/2014 | Reschke et al. |
| 2014/0228844 A1 | 8/2014 | Horlle et al. |
| 2014/0257284 A1 | 9/2014 | Artale |
| 2014/0303551 A1 | 10/2014 | Germain et al. |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133929 A1 | 5/2015 | Evans et al. |
| 2015/0141981 A1 | 5/2015 | Price et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0230861 A1 | 8/2015 | Woloszko et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2016/0317215 A1 | 11/2016 | Worrell et al. |

FOREIGN PATENT DOCUMENTS

| | | |
|---|---|---|
| DE | 19608716 C1 | 4/1997 |
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 2529681 A1 | 12/2012 |
| EP | 1767164 B1 | 1/2013 |
| EP | 2316359 B1 | 3/2013 |
| EP | 2090238 B1 | 4/2013 |
| EP | 2578172 A2 | 4/2013 |
| EP | 2508143 B1 | 2/2014 |
| GB | 2472216 A | 2/2011 |
| JP | H08229050 A | 9/1996 |
| JP | 2008018226 A | 1/2008 |
| JP | 5714508 B2 | 5/2015 |
| WO | 8103272 A1 | 11/1981 |
| WO | 9307817 A1 | 4/1993 |
| WO | 9322973 A1 | 11/1993 |
| WO | 9510978 A1 | 4/1995 |
| WO | 9635382 A1 | 11/1996 |
| WO | 9710764 A1 | 3/1997 |
| WO | 9800069 A1 | 1/1998 |
| WO | 9840020 A1 | 9/1998 |
| WO | 9857588 A1 | 12/1998 |
| WO | 9923960 A1 | 5/1999 |
| WO | 9940857 A1 | 8/1999 |
| WO | 9940861 A1 | 8/1999 |
| WO | 0024330 A1 | 5/2000 |
| WO | 0024331 A1 | 5/2000 |
| WO | 0025691 A1 | 5/2000 |
| WO | 0128444 A1 | 4/2001 |
| WO | 02062241 A1 | 8/2002 |
| WO | 02080797 A1 | 10/2002 |
| WO | 03001986 A2 | 1/2003 |
| WO | 03013374 A1 | 2/2003 |
| WO | 03020339 A2 | 3/2003 |
| WO | 03028541 A2 | 4/2003 |
| WO | 03030708 A2 | 4/2003 |
| WO | 03068046 A2 | 8/2003 |
| WO | 2004011037 A2 | 2/2004 |
| WO | 2004032754 A2 | 4/2004 |
| WO | 2004032762 A1 | 4/2004 |
| WO | 2004032763 A2 | 4/2004 |
| WO | 2004078051 A2 | 9/2004 |
| WO | 2004112618 A2 | 12/2004 |
| WO | 2005052959 A2 | 6/2005 |
| WO | 2006021269 A1 | 3/2006 |
| WO | 2006036706 A1 | 4/2006 |
| WO | 2006055166 A2 | 5/2006 |
| WO | 2006119139 A2 | 11/2006 |
| WO | 2008020964 A2 | 2/2008 |
| WO | 2008045348 A2 | 4/2008 |

(56) References Cited

FOREIGN PATENT DOCUMENTS

| | | |
|---|---|---|
| WO | 2008099529 A1 | 8/2008 |
| WO | 2008101356 A1 | 8/2008 |
| WO | 2009022614 A1 | 2/2009 |
| WO | 2009036818 A1 | 3/2009 |
| WO | 2009039179 A1 | 3/2009 |
| WO | 2009059741 A1 | 5/2009 |
| WO | 2009082477 A2 | 7/2009 |
| WO | 2009149234 A1 | 12/2009 |
| WO | 2010017266 A1 | 2/2010 |
| WO | 2010104755 A1 | 9/2010 |
| WO | 2011008672 A2 | 1/2011 |
| WO | 2011084768 A1 | 7/2011 |
| WO | 2011089717 A1 | 7/2011 |
| WO | 2011144911 A1 | 11/2011 |
| WO | 2012044606 A2 | 4/2012 |
| WO | 2012166510 A1 | 12/2012 |
| WO | 2013034629 A1 | 3/2013 |
| WO | 2013062978 A2 | 5/2013 |
| WO | 2013102602 A2 | 7/2013 |
| WO | 2013154157 A1 | 10/2013 |
| WO | 2015197395 A8 | 12/2015 |

OTHER PUBLICATIONS

Hörmann et al., "Reversible and irreversible denaturation of collagen fibers." Biochemistry, 10, pp. 932-937 (1971).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Lee et al., "A multi-sample denaturation temperature tester for collagenous biomaterials," Med. Eng. Phy., vol. 17, No. 2, pp. 115-121 (Mar. 1995).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Humphrey, J.D., "Continuum Thermomechanics and the Clinical Treatment of Disease and Injury," Appl. Mech. Rev., vol. 56, No. 2 pp. 231-260 (Mar. 2003).

Covidien Brochure, The LigaSure™ 5 mm Blunt Tip Sealer/Divider Family, dated Apr. 2013 (2 pages).

Douglas, S.C. "Introduction to Adaptive Filter". Digital Signal Processing Handbook. Ed. Vijay K. Madisetti and Douglas B. Williams. Boca Raton: CRC Press LLC, 1999.

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

U.S. Appl. No. 15/258,578, filed Sep. 7, 2016.

U.S. Appl. No. 12/576,529, filed Oct. 9, 2009.

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Moran et al., "Thermally Induced Shrinkage of Joint Capsule," Clinical Orthopaedics and Related Research, No. 281, pp. 248-255 (Dec. 2000).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Kurt Gieck & Reiner Gieck, Engineering Formulas § Z.7 (7th ed. 1997).

Glaser and Subak-Sharpe, Integrated Circuit Engineering, Addison-Wesley Publishing, Reading, MA (1979). (book—not attached).

Covidien Brochure, [Value Analysis Brief], LigaSure Advance™ Pistol Grip, dated Rev. Apr. 2010 (7 pages).

Covidien Brochure, The LigaSure Precise™ Instrument, dated Mar. 2011 (2 pages).

U.S. Appl. No. 15/265,293, filed Sep. 14, 2016.

U.S. Appl. No. 15/258,598, filed Sep. 7, 2016.

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Wall et al., "Thermal modification of collagen," J Shoulder Elbow Surg, No. 8, pp. 339-344 (Jul./Aug. 1999).

National Semiconductors Temperature Sensor Handbook—http://www.national.com/appinfo/tempsensors/tiles/temphb.pdf; accessed online: Apr. 1, 2011.

Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.

Jang, J. et al. "Neuro-fuzzy and Soft Computing." Prentice Hall, 1997, pp. 13-89, 199-293, 335-393,453-496, 535-549.

Henriques. F.C., "Studies in thermal injury V. The predictability and the significance of thermally induced rate processes leading to irreversible epidermal injury." Archives of Pathology, 434, pp. 489-502 (1947).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Chen et al., "Heat-Induced Changes in the Mechanics of a Collagenous Tissue: Isothermal Free Shrinkage," Transactions of the ASME, vol. 119, pp. 372-378 (Nov. 1997).

Wright, et al., "Time-Temperature Equivalence of Heat-Induced Changes in Cells and Proteins," Feb. 1998. ASME Journal of Biomechanical Engineering, vol. 120, pp. 22-26.

Sullivan, "Optimal Choice for Number of Strands in a Litz-Wire Transformer Winding," IEEE Transactions on Power Electronics, vol. 14, No. 2, Mar. 1999, pp. 283-291.

U.S. Appl. No. 15/258,570, filed Sep. 7, 2016.

U.S. Appl. No. 15/258,586, filed Sep. 7, 2016.

Leonard I. Malis, M.D., "The Value of Irrigation During Bipolar Coagulation," 1989.

\* cited by examiner

END EFFECTOR WITH DETECTABLE CONFIGURATIONS

BACKGROUND

The present disclosure relates to surgical instruments and, in various circumstances, to surgical sealing and transecting instruments.

SUMMARY

In one embodiment, a surgical end effector includes a first jaw comprising a first electrode and a second jaw, wherein at least one of the first jaw and the second jaw is movable relative to the other one of the first jaw and the second jaw to transition the end effector between an open configuration, an approximated configuration, and a fully approximated configuration. The second jaw includes a second electrode and at least one spacer extending from the second electrode, wherein the at least one spacer is configured to maintain a minimum predetermined distance between the first electrode and the second electrode when the end effector is in the fully approximated configuration, wherein the at least one spacer is in contact with the first electrode in the fully approximated configuration, wherein the at least one spacer is spaced apart from the first electrode in the open configuration, and wherein the at least one spacer is comprised of a semi-conductive material.

In one embodiment, a surgical instrument includes an end effector that includes a first jaw comprising a first electrode and a second jaw, wherein at least one of the first jaw and the second jaw is movable relative to the other one of the first jaw and the second jaw to transition the end effector between an open configuration, an approximated configuration, and an fully approximated configuration. The second jaw includes a second electrode, wherein tissue is captured between the first electrode and the second electrode in the approximated configuration and at least one spacer extending from the second electrode, wherein the at least one spacer is configured to maintain a minimum predetermined distance between the first electrode and the second electrode when the end effector is in the fully approximated configuration, and wherein the at least one spacer is simultaneously in contact with the first electrode and the second electrode in the fully approximated configuration The surgical instrument further includes a switch configured to control energy transmission between the first electrode and the second electrode, wherein the switch is activatable to permit energy transmission between the first electrode and the second electrode and a circuit. The circuit is operable to: detect activation of the switch, detect an impedance between the first electrode and the second electrode in response to the activation of the switch, generate a first response corresponding to the open configuration of the end effector when the impedance is greater than or equal to a predetermined threshold, generate a second response corresponding to the approximated configuration of the end effector when the impedance is in a first range of impedance, and generate a third response corresponding to the fully approximated configuration when the impedance is in a second range of impedance different from the first range of impedance.

BRIEF DESCRIPTION OF THE DRAWINGS

The features and advantages provided in this disclosure, and the manner of attaining them, will become more apparent and the disclosure itself will be better understood by reference to the following description of instances of the disclosure taken in conjunction with the accompanying drawings, wherein.

Corresponding reference characters indicate corresponding parts throughout the several views. The examples set out herein illustrate various embodiments of the disclosure, in one form, and such examples are not to be construed as limiting the scope of the disclosure in any manner.

DETAILED DESCRIPTION

Figure 1:
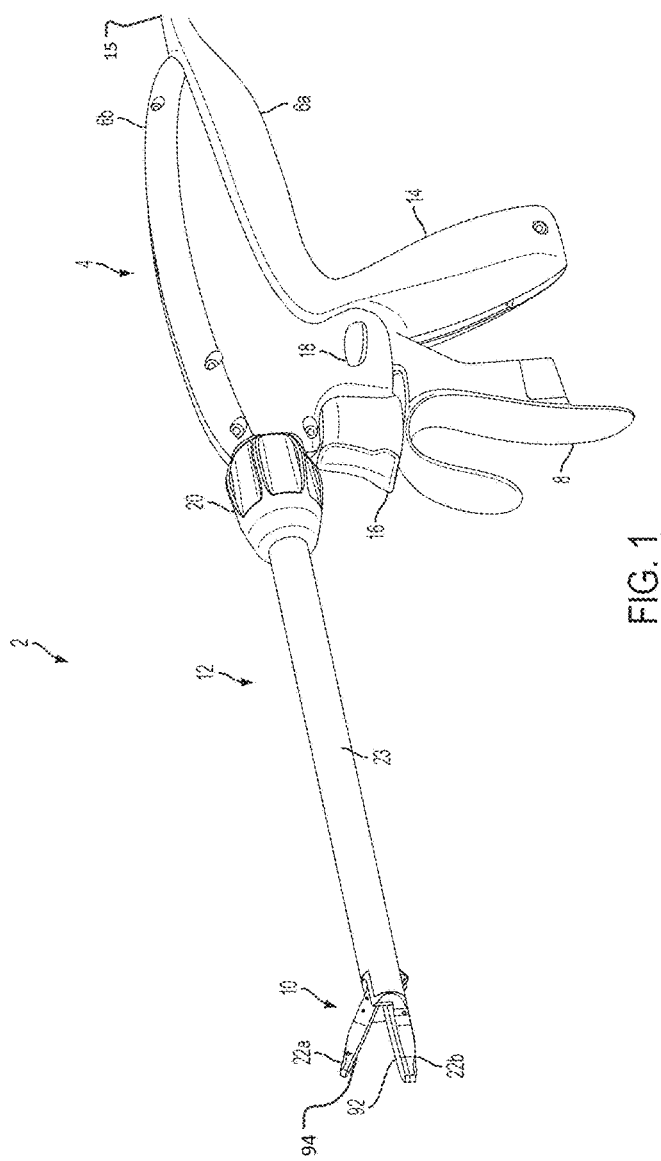
FIG. 1 illustrates a perspective view of a surgical instrument comprising a handle and an end effector.

Certain example embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting example embodiments and that the scope of the various embodiments of the present disclosure is defined solely by the claims. The features illustrated or described in connection with one example embodiment may be combined with the features of other embodiments. Such modifications and variations are intended to be included within the scope of the present disclosure.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various example devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 2:
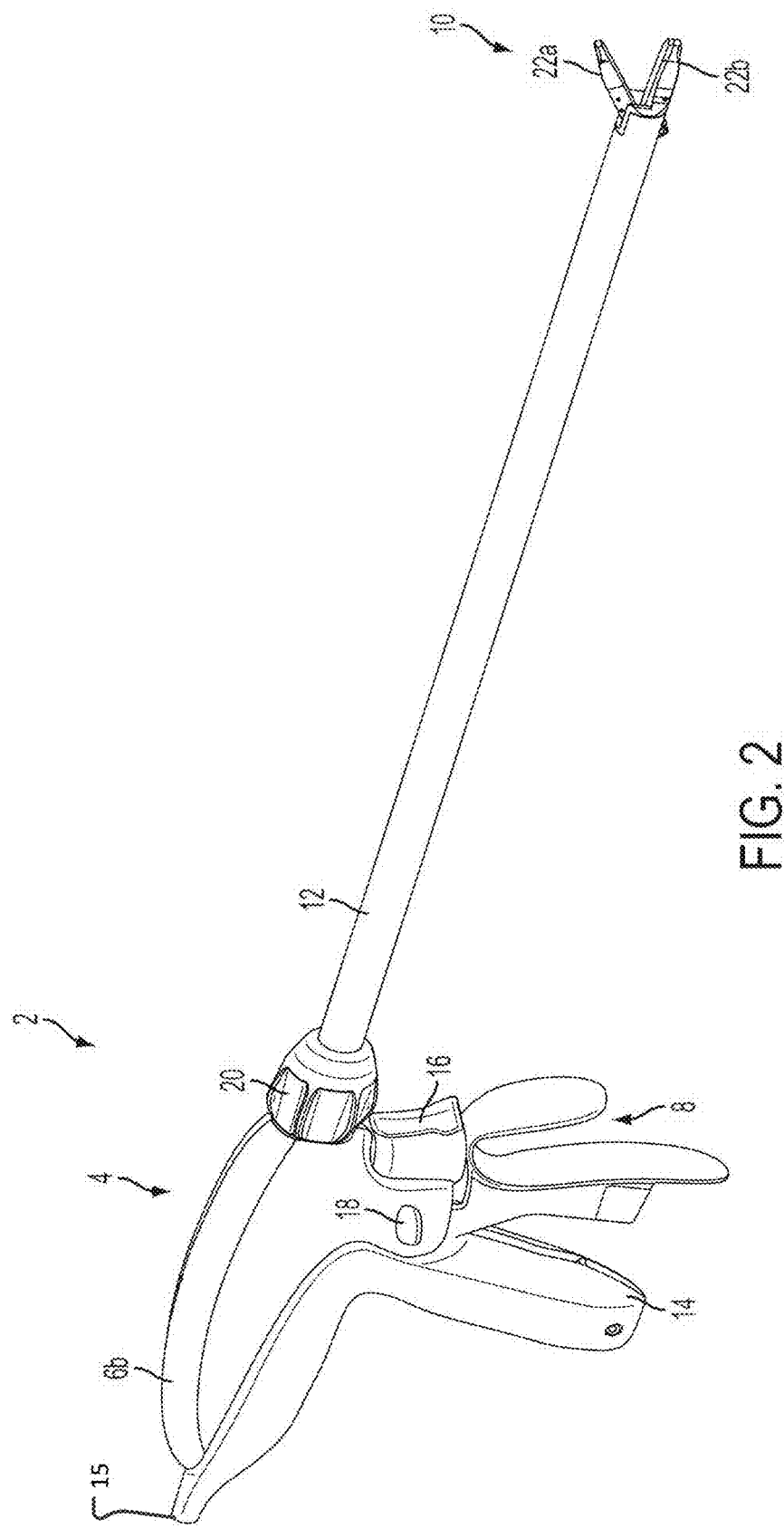
FIG. 2 illustrates a perspective view of the surgical instrument of FIG. 1, according to one embodiment.
Figure 3:
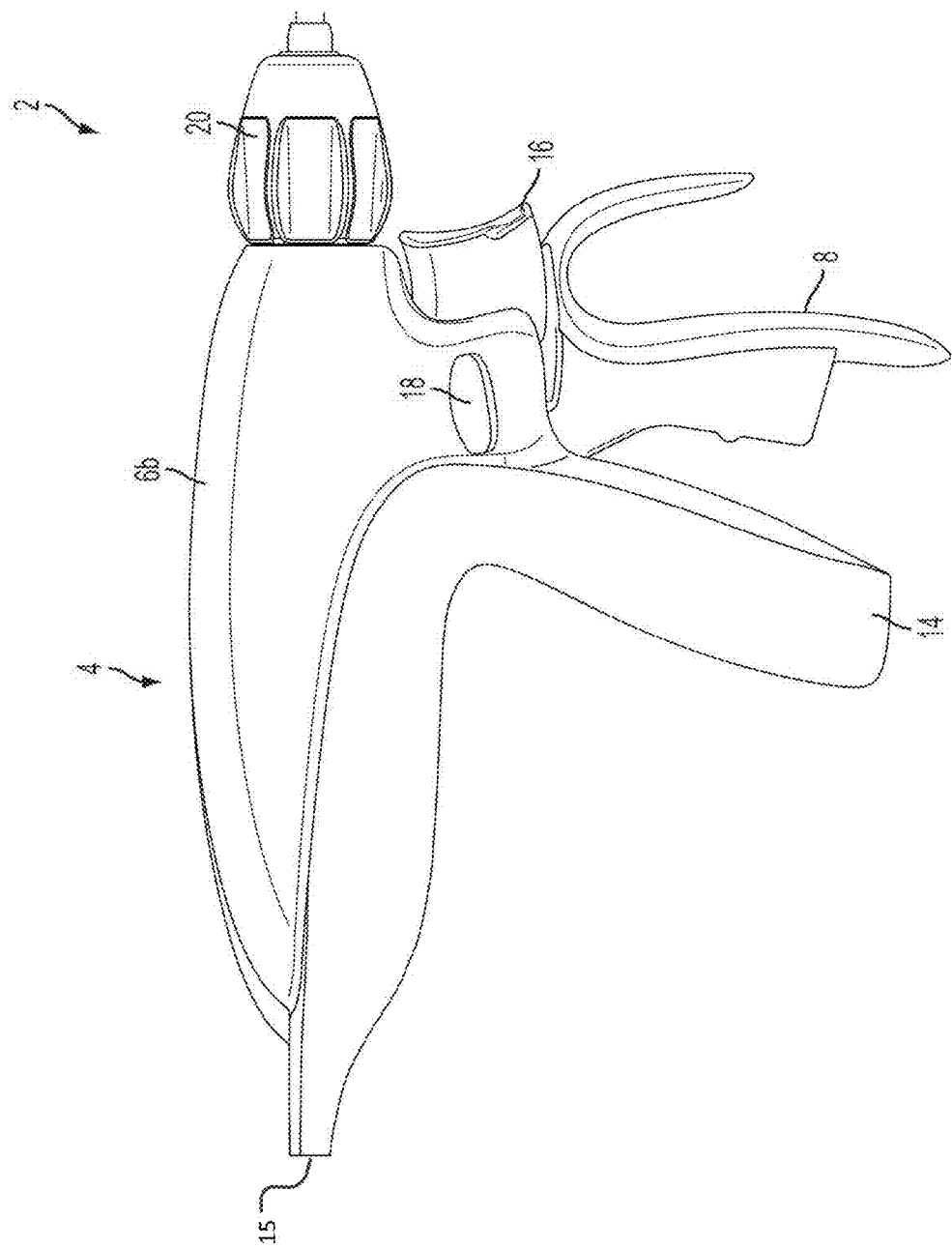
FIG. 3 illustrates a side-elevational view of the handle of the surgical instrument of FIG. 1, according to one embodiment.

FIG. 1 illustrates a perspective view of a surgical instrument 2 comprising a handle assembly 4 and an end effector 10 according to one embodiment. FIG. 2 illustrates a perspective view of the surgical instrument 2 of FIG. 1 according to one embodiment and FIG. 3 illustrates a side-elevational view of the handle assembly 4 of the surgical instrument of FIG. 1 according to one embodiment. Turning to FIGS. 1-3, one form of an electrosurgical instrument 2 is depicted. The electrosurgical instrument 2 comprises a handle assembly 4, a shaft assembly 12 coupled to a distal end of the handle assembly 4, and an end effector 10 coupled to the distal end of the shaft assembly 12. The handle assembly 4 is configured as a pistol grip and comprises a left handle housing shroud 6a, a right handle housing shroud 6b, a closure trigger 8, a pistol-grip handle 14, a firing trigger 16, an energy button 18, and a rotatable shaft knob 20. An electrical cable may enter the handle assembly 4 at a proximal end 15.

In some circumstances, the end effector 10 can be coupled to the distal end of the shaft assembly 12. The end effector 10 may include a first jaw 22a and a second jaw 22b. The first jaw 22a can be pivotably coupled to the second jaw 22b. The first jaw 22a is moveable with respect to the second jaw 22b to grasp tissue therebetween. In some circumstances, the second jaw 22b is fixed. In other circumstances, the first jaw 22a and the second jaw 22b are pivotably movable with respect to each other. The end effector 10 may include one or more electrodes such as, for example, electrode 92, 94. The electrodes 92, 94 can be configured to pass energy through tissue positioned between the electrodes 92, 94. Energy delivered by the electrodes 92, 94 may comprise, for example, radiofrequency (RF) energy, sub-therapeutic RF energy, therapeutic RF energy, ultrasonic energy, and/or other suitable forms of energy. In some circumstances, a cutting member (not shown) is receivable within a longitudinal slot 40 (FIG. 4) defined by the first jaw 22a and/or the second jaw 22b. The cutting member can be configured to cut tissue grasped between the first jaw 22a and the second jaw 22b. In some circumstances, the cutting member may include an electrode for delivering energy, such as, for example, RF and/or ultrasonic energy.

In certain instances, an energy button 18 is configured to deliver energy to the at least one electrode 92 from a power source. In certain instances, when the energy button 18 is depressed, a circuit is completed allowing delivery of energy to the electrode 92. In some embodiments, the power source is a generator. In certain instances, the generator is external to the surgical instrument 2 which is separably coupled to the generator. In other instances, the generator is integrated with the surgical instrument 2. In certain instances, the power source may be suitable for therapeutic tissue treatment, tissue cauterization/sealing, as well as sub-therapeutic treatment and measurement.

In certain instances, the surgical instrument 2 may include a closure drive assembly which may comprise an outer sheath 23, for example. In certain instances, the closure trigger 8 can be operatively coupled to at least one of the jaws 22a, 22b through the closure drive assembly such that actuation of the closure trigger 8 in a closure stroke may transition the jaws 22a, 22b between a plurality of configurations including an open configuration, an approximated configuration, and a fully approximated configuration, for example. In certain instances, the surgical instrument 2 may include a firing drive assembly. In certain instances, the firing trigger 16 may be operatively coupled to the cutting member of the end effector 10 through the firing drive assembly such that actuation of the firing trigger 16 in a firing stroke may cause the cutting member to be advanced relative to the end effector 10 to cut tissue captured between the jaws 22a, 22b, for example.

When electrical current is supplied to an electrode such as, for example, the electrodes 92 and/or 94, the electrical current can pass through the tissue in electrical communication with the surrounding electrodes 92 and/or 94, for example. In one instance, the electrical current can pass through the tissue positioned against and/or surrounding the electrode 92 and/or 94, for example. In various circumstances, the current flowing through the electrode can generate heat within the electrode and the surrounding tissue. In certain circumstances, the heat can denature proteins within the tissue and, in co-operation with clamping pressure provided by the jaws 22a, 22b of the end effector 10, the denatured proteins can form a seal within the tissue, for example.

FIG. 2 illustrates a side perspective view of the electrosurgical instrument 2 illustrated in FIG. 1. FIG. 2 illustrates the right handle housing shroud 6b. The energy button 18 may extend through the handle assembly 4 and is accessible on both sides of the handle assembly 4. The closure trigger 8, the firing trigger 16, and the energy button 18 may comprise an ergonomic design. In some circumstances, the handle assembly 4 is thinner near the energy button 18 to allow ease of access to the energy button 18 by a clinician. In some circumstances, the energy button 18 is disposed on either the left handle housing 6a or the right handle housing shroud 6b. FIG. 3 illustrates a side view of the electrosurgical instrument 2 and the right handle housing shroud 6b.

Various electrosurgical instruments suitable for use with the present disclosure are described in U.S. patent application Ser. Nos. 14/075,839 and 14/075,863.

Referring to FIGS. 4-8, FIG. 4 illustrates an end effector 10 in an open configuration according to one embodiment. The end effector 10 includes one or more spacers 50 configured to maintain a minimum predetermined distance between the electrodes 92, 94. As described above, the closure trigger 8 can be operatively coupled to at least one of the jaws 22a, 22b through the closure drive assembly such that actuation of the closure trigger 8 in a closure stroke may transition the end effector 10 between a plurality of configurations.

Figure 6:
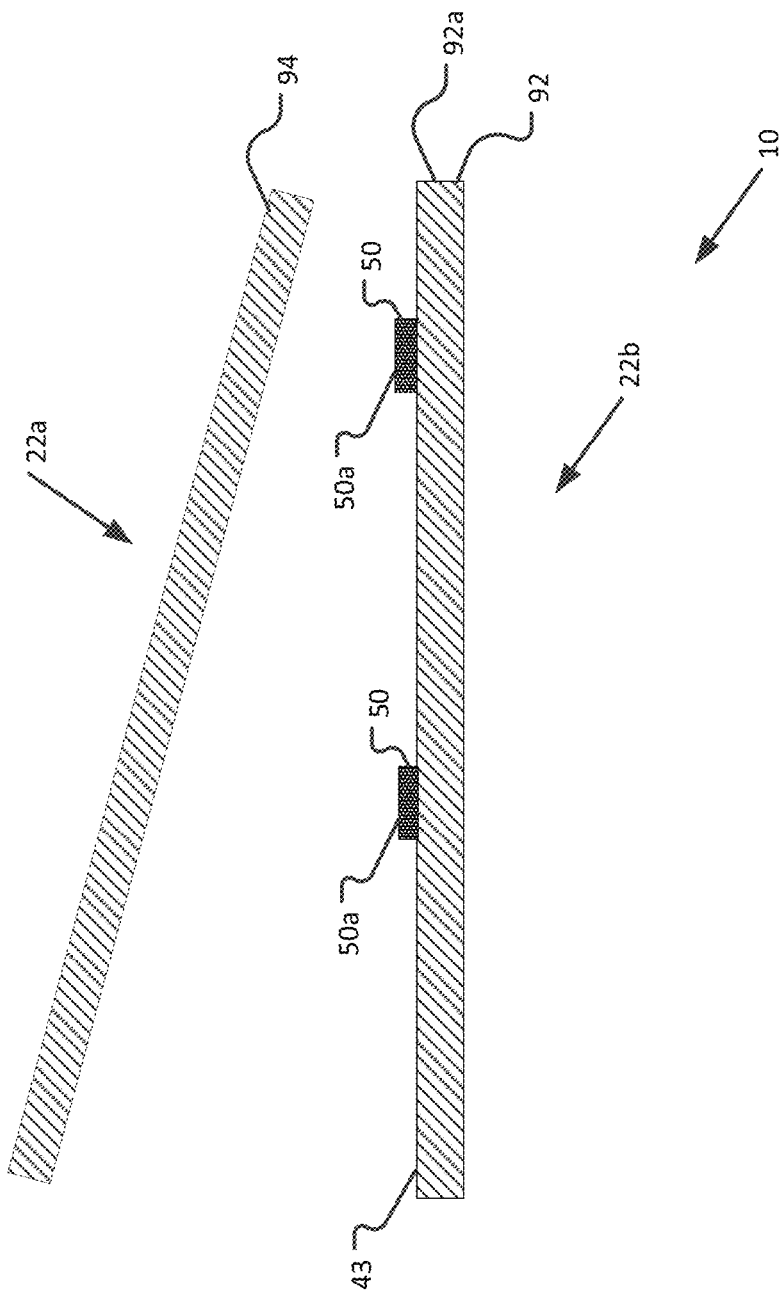
FIG. 6 illustrates a partial cross sectional view of the electrodes of the surgical instrument of FIG. 1 in an open configuration, according to one embodiment.
Figure 7:
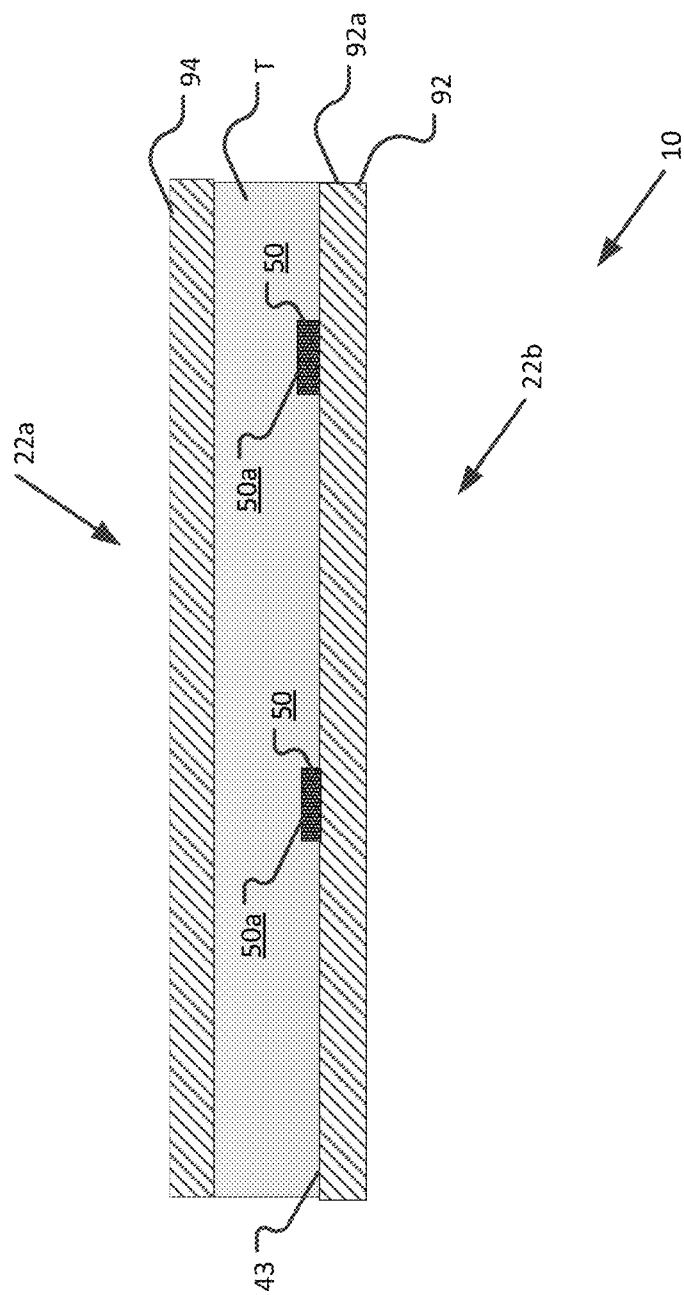
FIG. 7 illustrates a partial cross sectional view of the electrodes of the surgical instrument of FIG. 1 in an approximated configuration with tissue disposed between the electrodes, according to one embodiment.
Figure 8:
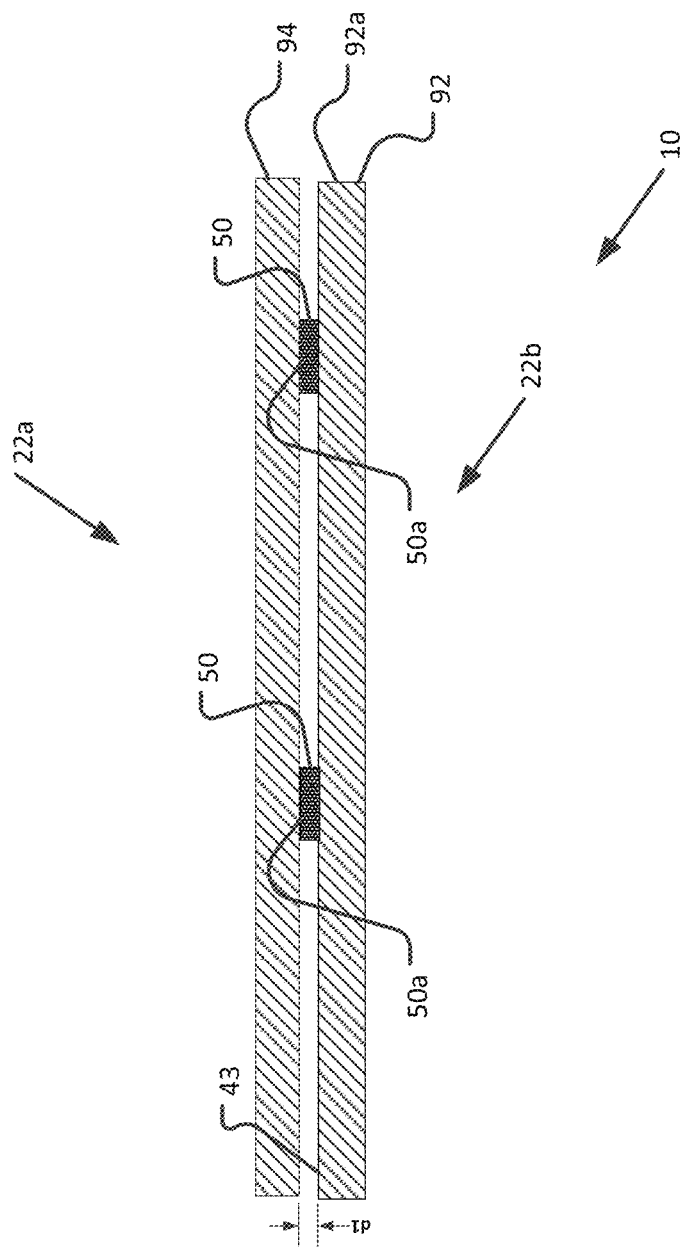
FIG. 8 illustrates a partial cross sectional view of the electrodes of the surgical instrument of FIG. 1 in a fully approximated configuration with a plurality of spacers maintaining a minimum predetermined distance between the electrodes, according to one embodiment.

FIG. 6 illustrates a partial cross sectional view of the electrodes 92, 94 in an open configuration, according to one embodiment. FIG. 7 illustrates a partial cross section view of the electrodes 92, 94 in an approximated configuration, according to one embodiment. FIG. 8 illustrates a partial cross sectional view of the electrodes 92, 94 in a fully approximated configuration, according to one embodiment. In certain instances, the end effector 10 may include an open configuration wherein the electrodes 92, 94 are spaced apart and the spacers 50 are in contact with only one of the electrodes 92, 94, as illustrated in FIG. 6. In certain instances, the end effector 10 may comprise an approximated configuration, as illustrated in FIG. 7, wherein tissue is captured between the electrodes 92, 94, and wherein the spacers 50 are in contact with only one of the electrodes 92, 94.

Further to the above, the end effector 10 may also comprise a fully approximated configuration, wherein the spacers 50 are in electrical contact with the electrodes 92, 94. In one instance, the spacers 50 may be in direct electrical contact with the electrodes 92, 94. In the fully approximated configuration the spacers 50 may maintain a gap between the electrodes 92, 94, as illustrated in FIG. 8. The size of the gap between the electrodes 92, 94 in the fully approximated configuration may depend in part on the height, e.g., thickness, of the spacers 50. In one instance, the electrodes 92, 94 are allowed to fully close uninterrupted in the fully approximated configuration, which causes one or more of the spacers 50 to be in electrical contact with the electrode 92 and the electrode 94 simultaneously.

In certain instances, as illustrated in FIG. 8, a spacer 50 can prevent, or at least resist, electrical contact between the electrode 92 and the electrode 94 in the fully approximated configuration. In certain instances, depressing or activating the energy button 18 while the electrodes 92, 94 are in electrical contact with each other may yield a short circuit. In certain instances, one or more of the spacers 50 can create a barrier between the electrode 92 and the electrode 94 to avoid circuit shorting in the event the energy button 18 is depressed while the end effector 10 is in the fully approximated configuration.

Figure 4:
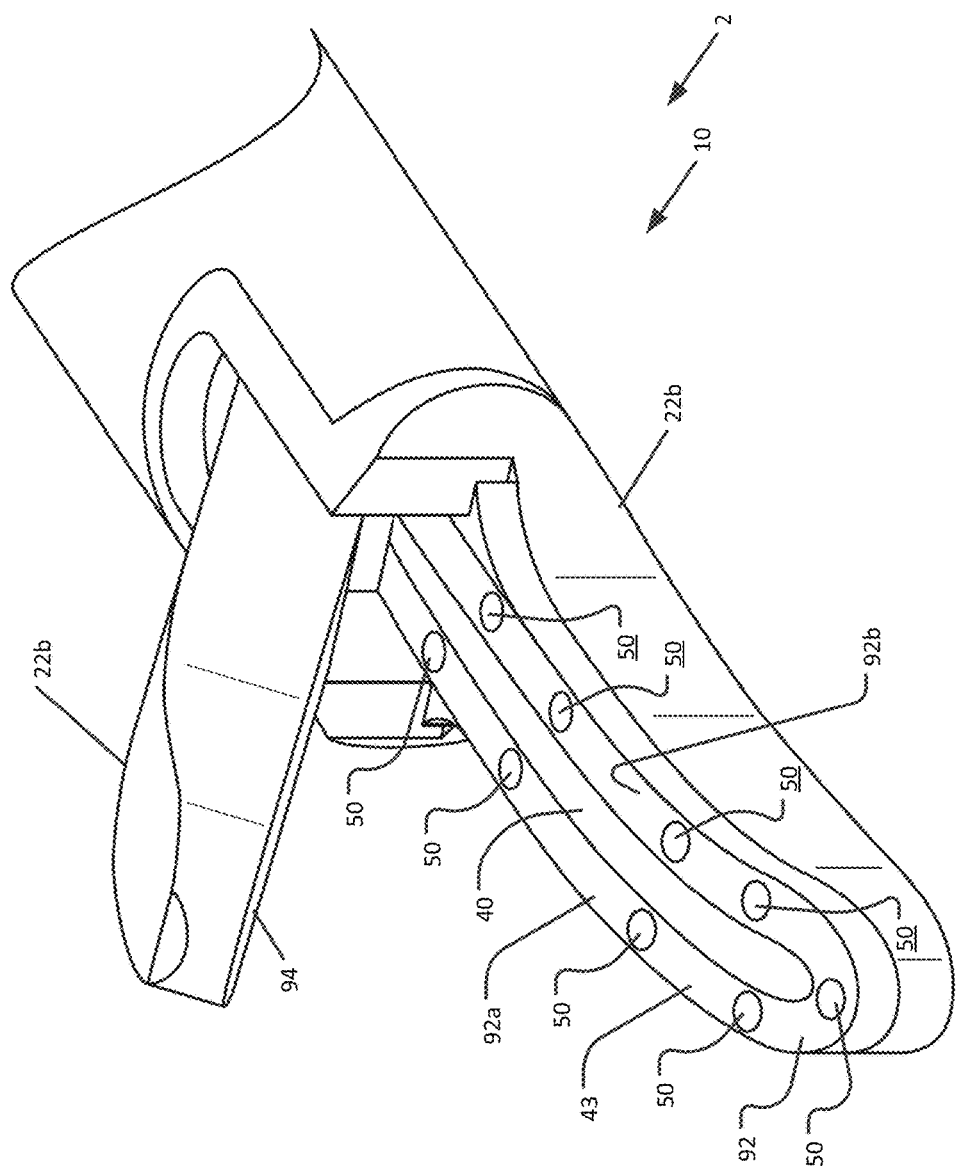
FIG. 4 illustrates a perspective view of an end effector of the surgical instrument of FIG. 1, according to one embodiment.
Figure 5:
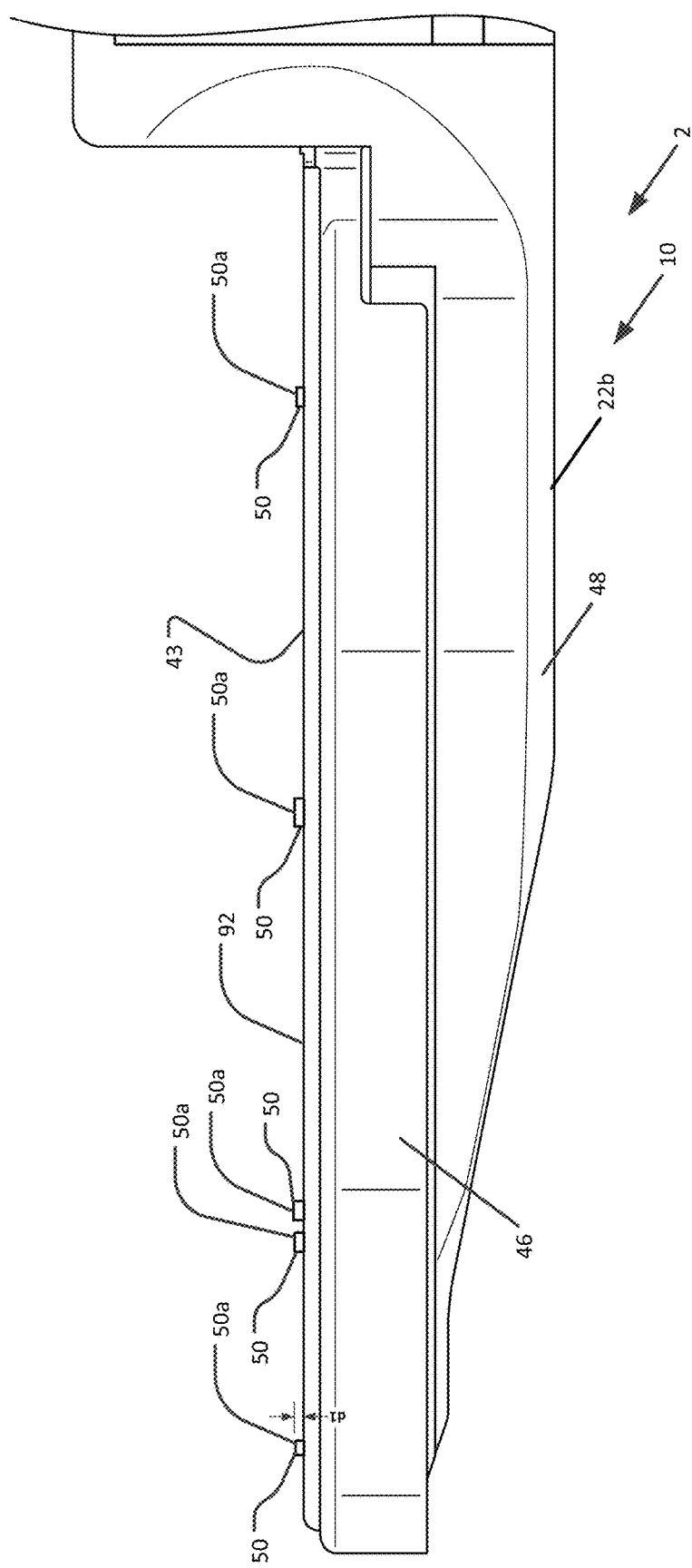
FIG. 5 illustrates a side-elevational view of a jaw of the end effector of the surgical instrument of FIG. 1, according to one embodiment.

FIG. 4 illustrates one embodiment of the end effector 10 in an open configuration. As illustrated in FIG. 4, the spacers 50 can be attached to the electrode 92, for example. In the fully approximated configuration, the electrode 94 may rest against one or more of the spacers 50, as illustrated in FIG. 8. In one example, the spacers 50 can be disposed onto the electrode 92 and may extend from an outer surface 43 of the electrode 92. A spacer 50 can be attached to the outer surface 43. For example, the spacer 50 can be glued onto the outer surface 92. Other techniques for attaching the pacer 50 to the outer surface 43 are contemplated by the present disclosure. For example, the electrode 92 may comprise a socket (not shown) configured to partially receive a spacer 50. In other words, the spacer 50 can be partially embedded in the socket of the electrode 92.

As illustrated in FIG. 4, the spacers 50 may be positioned at any suitable interval along the length of the electrode 92. In some examples, including the one shown in FIG. 4, the spacers 50 may be arranged in pairs, with each pair straddling the longitudinal slot 40. In various instances, the spacers 50 can be arranged in rows that extend in parallel, or at least substantially in parallel, with the elongate slot 40. For example, as illustrated in FIG. 4, a first row of the spacers 50 and a second row of the spacers 50 may be disposed on opposite lateral sides of the elongate slot 40. In certain instances, the spacers 50 can be in any array, offset, laterally across from one another, or staggered along a length of one or both of the jaws 22a, 22b.

Referring to FIG. 8, a spacer 50 may protrude or extend a predetermined distance (d1) above or beyond the outer surface 43 of the electrode 92. As illustrated in FIG. 8, a minimum predetermined gap between the electrodes 92, 94 in the fully approximated configuration can be defined by the predetermined distance (d1). The predetermined distance (d1) may correspond to a height of the spacers 50, for example. In certain instances, the predetermined distance (d1) can be any distance selected from a range of about 0.001 inch to about 0.010 inch. In certain instances, the predetermined distance (d1) can be any distance selected from a range of about 0.003 inch to about 0.008 inch. In certain instances, the predetermined distance (d1) can be about 0.004 inch, for example. In certain instances, the predetermined distance (d1) can be about 0.005 inch, for example.

In various instances, one or more of the spacers 50 can be comprised of one or more semi-conductive materials. In various instances, one or more of the spacers 50 can be comprised of a plastic material that is considered a static dissipative material. In certain instances, one or more of the spacers 50 can be comprised of one or more materials comprising a surface resistivity in a range of about $10^6$ to about $10^9$ ohm/square, for example. In certain instances, one or more of the spacers 50 can be comprised of one or more materials comprising a surface resistivity in a range of about $10^7$ to about $10^8$ ohm/square, for example. In certain instances, one or more of the spacers 50 can be comprised of one or more materials comprising a surface resistivity of about $10^7$ ohm/square, for example. In certain instances, one or more of the spacers 50 can be comprised of one or more materials comprising a surface resistivity of about $10^8$ ohm/square, for example.

In certain instances, one or more of the spacers 50 can be comprised of one or more materials comprising a surface resistivity in a range of about $10^2$ to about $10^6$ ohm/square, for example. In certain instances, one or more of the spacers 50 can be comprised of one or more materials comprising a surface resistivity in a range of about $10^3$ to about $10^5$ ohm/square, for example. In certain instances, one or more of the spacers 50 can be comprised of one or more materials comprising a surface resistivity of about $10^3$ ohm/square, for example. In certain instances, one or more of the spacers 50 can be comprised of one or more materials comprising a surface resistivity of about $10^4$ ohm/square, for example. The reader will appreciate that a selection of the material composition of the spacer 50 depends, at least in part, on the size and shape of the spacers 50 and the method of determining impedance across the electrodes through the spacers. The reader will appreciate that a selection of the material composition of the spacer 50 takes into consideration that the resistance of the spacers 50 need to be sufficiently high to distinguish between a closed configuration and a short circuit, for example.

In certain instances, one or more of the spacers 50 can be comprised of one or more materials including ABS, Acetal, PEEK, Polycarbonate, Polypropylene, PDVF, UHMW-PE, and Polyamide filled with carbon powder, carbon fiber, or stainless steel. These fillers may in some instances be about 15% of the total weight. In certain instances, the fillers can be about 17% of the total weight. In certain instances, the fillers can be about 18% of the total weight. In certain instances, the fillers can be about 19% of the total weight. In certain instances, the fillers can be about 20% of the total weight. Other values of the material-to-filler ratio are contemplated by the present disclosure. Some of the suitable materials for the spacers 50 comprise the trade names HYDEL, TECAFORM, TECAPEEK, SINTIMID, SEMITRON, POMALUX, TIVAR, STATICON, KYDEX, and ABSYLUX, for example.

The following table provides a list of suitable materials for use with the present disclosure. The reader will appreciate, however, that the list of materials presented in the following table is not exhaustive and that the spacers 50 may be comprised of other materials, as described above.

| Supplier | Name |
| --- | --- |
| EMS | Grivory XE 4027 |
| EMS | Grivory GV-5H |
| EMS | Grivory HTV-3H1 |
| EMS | Grivory HT2V-3H |
| Solvay | Ixef 1524 |
| Solvay | Ixef 1022 |
| Solvay | Amodel HFFR-4133 |
| Technical Polymers | Thermec N 5350R30F4H2 Bk-1 |
| Technical Polymers | Thermec N 5357R30F4H2 Bk-1 |
| PBI Products | Celazole TF-60V |
| Dupont | Zytel HTN FR52G30 NHF BK337 |

In certain instances, one or more of the spacers 50 can be comprised, or at least partially comprised, of a material with temperature dependent impedance. For example, a spacer 50 can be comprised, or at least partially comprised, of a positive temperature coefficient (PTC) thermistor, wherein impedance of the spacer 50 increases over a period of time in response to an increase in temperature of the spacer 50. As current flows through tissue captured between the electrodes 92, 94, the temperature of the tissue may increase which may increase the temperature of the spacer 50. As the temperature of the spacer 50 increases, the impedance of the spacer 50 may increase. In such instances, the current passing through the spacer 50 may decrease over time in response to the increase in the impedance of the spacer 50 resulting from the increased temperature of the spacer 50. Initially, the current passing through the spacer 50 may be sufficiently large to treat and/or seal tissue in contact, or at least partially in contact, with the spacer 50. As the temperature of the spacer 50 increases the current passing through the spacer 50 my decrease due to the increase in the impedance of the spacer 50, for example.

In another example, a spacer 50 can be comprised, or at least partially comprised, of a negative temperature coefficient (NTC) thermistor, wherein impedance of the spacer 50 decreases over a period of time in response to an increase in temperature of the spacer 50. As current flows through tissue captured between the electrodes 92, 94, the temperature of the tissue may increase which may increase the temperature of the spacer 50. As the temperature of the spacer 50 increases, the impedance of the spacer 50 may decrease. In such instances, the current passing through the spacer 50 may increase over time in response to the decrease in the impedance of the spacer 50 resulting from the decreased temperature of the spacer 50. Initially, limited or no current may pass through the spacer 50. As the temperature of the spacer 50 increases the current passing through the spacer 50 my increase due to the decrease in the impedance of the spacer 50, for example.

In certain instances, the semi-conductive spacers 50 can permit a limited current to flow between the electrodes 92, 94 through the semi-conductive spacers 50 when the semi-conductive spacers 50 are in electrical contact with the electrodes 92, 94 in the fully approximated configuration. In such instances, the limited current may flow through the semi-conductive spacers 50 when the energy button 18 is depressed while the electrode 92 and the electrode 94 are in contact with the semi-conductive spacers 50, for example. Said another way, the limited current may flow through the semi-conductive spacers 50 when the energy button 18 is depressed while the electrode 94 is rested against the semi-conductive spacers 50, for example.

In certain instances, a semi-conductive spacer 50 can act as a conduit for transmitting limited energy between the electrodes 92, 94 when the energy button 18 is depressed or activated while the electrodes 92, 94 are in contact with the semi-conductive spacer 50 in the fully approximated configuration, for example. In certain instances, as described above, a semi-conductive spacer 50 can be attached to the electrode 92, for example. In such instances, the limited energy may be transmitted between the electrodes 92, 94 when the energy button 18 is depressed or activated while the electrode 94 is rested against the semi-conductive spacer 50 that is attached to the electrode 92. In one example, the limited energy is in the form of current that flows between the electrodes 92, 94 through the semi-conductive spacer 50.

As described above, the end effector 10 can be transitioned between a plurality of configurations including, for example, an open configuration, as illustrated in FIG. 6, an approximated configuration, as illustrated in FIG. 7, and a fully approximated configuration, as illustrated in FIG. 8. Also as described above, the energy switch 18 can be activated while the end effector is in the approximated configuration to treat, seal, and/or cut tissue captured by the end effector 10 in the approximated configuration, for example. In certain instances, however, it may not be desirable to activate the energy switch 18 such as, for example, while the end effector 10 is in the open configuration or the fully approximated configuration. The present disclosure provides a method for detecting activation of the energy switch 18 and determining the configuration of the end effector 10 in response to the activation of the energy switch 18. The method further comprises generating a response suitable with the determined configuration of the end effector 10.

In certain instances, an activation circuit (not shown) can be employed to detect activation of the energy switch 18, as described in greater detail below. In certain instances, electrical energy transmission between the electrodes 92, 94, in response to activation of the energy switch 18, can be monitored to determine whether the end effector 10 is in the open configuration, the approximated configuration, or the fully approximated configuration. In one example, the energy transmission between the electrodes 92, 94 can be assessed by monitoring an impedance (Z) between the electrodes 92, 94. In one example, the energy transmission between the electrodes 92, 94 can be assessed by monitoring current flow between the electrodes 92, 94. Various sensing and/or monitoring devices can be employed to assess the energy transmission between the electrodes 92, 94.

In certain instances, when no electrical energy is transmitted between the electrodes 92, 94 in response to activation of the energy switch 18, it can be concluded that the end effector 10 is in the open configuration. In certain instances, when electrical energy is transmitted between the electrodes 92, 94 in response to activation of the energy switch 18 at an energy transmission rate that is in a first range of energy transmission rates, it can be concluded that the end effector 10 is in an approximated configuration. In certain instances, when electrical energy is transmitted between the electrodes 92, 94 in response to activation of the energy switch 18 at an energy transmission rate that is in a second range of energy transmission rates, different from the first range of energy transmission rates, it can be concluded that the end effector 10 is in a fully approximated configuration, for example.

Figure 9:
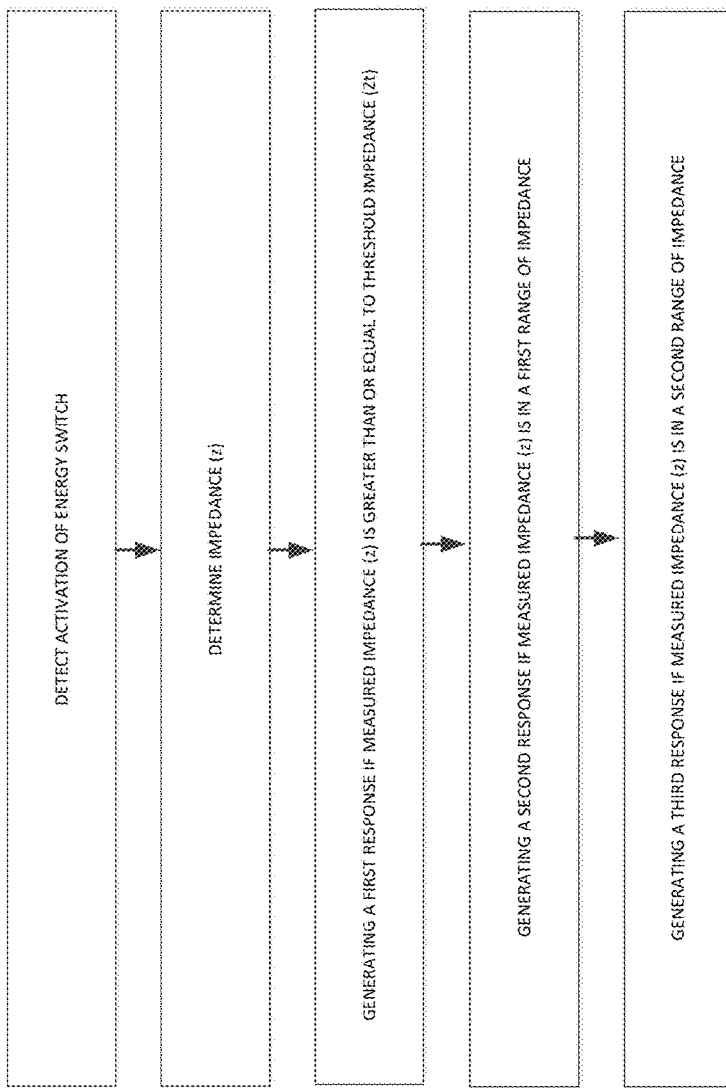
FIG. 9 illustrates a logic diagram, according to one embodiment.

FIG. 9 is a logic diagram for determining whether an end effector 10 is in the open configuration, the approximated configuration, or the fully approximated configuration and generating an appropriate response based on the outcome of the determination. As described above, whether electric energy is transmitted between the electrodes 92, 94 and its transmission rate can indicate the configuration of the end effector 10 following activation of the energy switch 18. In the example depicted in FIG. 9, the energy transmission between the electrodes 92, 94 is assessed by measuring an impedance (Z) between the electrodes 92, 94. Alternatively, current and/or voltage can be measured instead to assess the electric energy transmission between the electrodes 92, 94 or to assess the rate of change of electric energy transmission, e.g., power, between the electrodes 92, 94. In any event, the logic diagram depicted in FIG. 9 comprises detecting activation of the energy switch 18, measuring an impedance (Z) between the electrodes 92, 94, generating a first response when the measured impedance (Z) is greater than or equal to a predetermined threshold impedance (Zt), generating a second response when the measured impedance (Z) is in a first range of impedance, and generating a third response when the measured impedance (Z) is in a second range of impedance different from the first range of impedance.

In certain instances, when the value of the measured impedance (Z) is greater than or equal to a predetermined threshold impedance (Zt), an electric/electronic conduit (circuit) can be configured to determine that the end effector 10 is in an open configuration. In other words, when the value of the measured impedance (Z) is greater than or equal to the predetermined threshold impedance (Zt), the circuit can be configured to determine that the electrodes 92, 94 are spaced apart from each other with no tissue disposed therebetween. In such instances, a first response may be generated by the surgical instrument 2. The first response may comprise an alert response and/or an action response. In at least one example, the first response may comprise an error signal. In at least one example, the first response may comprise deactivating the energy switch 18. In at least one example, the first response may comprise alerting a user to deactivate or release the energy switch 18. In at least one example, the first response may comprise deactivating an energy source connected to the energy switch 18. In at least one example, the first response may comprise alerting the user that the end effector 10 is in the open configuration. In certain instances, the first response may comprise providing the user with instructions to capture tissue with the end effector 10 before reactivating the energy switch 18, for example.

In certain instances, the threshold impedance (Zt) can be greater than or equal to about 2100 ohms. In certain instances, the threshold impedance (Zt) can be greater than or equal to about 3000 ohms, for example. In certain instances, the threshold impedance (Zt) can be greater than or equal to about 4000 ohms, for example.

In certain instances, when the value of the measured impedance (Z) is in a first range of impedance, it can be concluded that the end effector 10 is in an approximated configuration. In other words, when the value of the measured impedance (Z) is in the first range of impedance, it can be concluded that tissue is captured between the electrodes 92, 94. In such instances, a second response can be generated by the surgical instrument 2. The second response can be an alert response and/or an action response. In at least one example, the second response comprises alerting a user that current is flowing through the captured tissue. In at least one example, the second response may comprise allowing current to continue to flow through the captured tissue until the energy switch 18 is released, for example. In at least one example, the second response comprises not deactivating the energy switch 18.

In certain instances, the first range of impedance may correspond to the impedance of tissue captured between the electrodes 92, 94 as current flows through the captured tissue. Typically, tissue impedance is in a range of about 3 ohms to about 400 ohms, for example. In at least on example, the first range of impedance can be selected from a range of about 1 ohm to about 499 ohms. In at least on example, the first range of impedance can be about 3 ohms to about 400 ohms. In at least on example, the first range of impedance can be about 100 ohms to about 300 ohms. In at least on example, the first range of impedance can be about 200 ohms to about 400 ohms. Other values for the first range of impedance are contemplated by the present disclosure. Various types of tissue may comprise various ranges of tissue impedance. Accordingly, the first range of impedance can be selected based on the type of tissue to be treated, for example.

In certain instances, when the value of the measured impedance (Z) is in a second range of impedance, the circuit can be configured to determine that the end effector 10 is in a fully approximated configuration. In other words, when the value of the measured impedance (Z) is in the second range of impedance, the circuit can be configured of determine that the electrodes 92, 94 are simultaneously in contact with a spacer 50. In such instances, a third response may be generated by the surgical instrument 2. The third response may comprise an alert response and/or an action response. In at least one example, the third response may comprise an error signal. In at least one example, the third response may comprise deactivating the energy switch 18. In at least one example, the third response may comprise alerting a user to deactivate or release the energy switch 18. In at least one example, the third response may comprise deactivating an energy source connected to the energy switch 18. In at least one example, the third response may comprise alerting the user that the end effector 10 is in the fully approximated configuration, deactivating the energy switch 18, and/or instructing the user to open the jaws 22a, 22b and capture tissue with the end effector 10 before reactivating the energy switch 18, for example.

In certain instances, the second range of impedance may be defined by the impedance of a spacer 50 as current flows between the electrodes 92, 94 through the spacer 50 in the fully approximated configuration. In at least one example, as described above, the spacer 50 may be comprised, or at least partially comprised, of a semi-conductive material. A semi-conductive spacer 50 may comprise an impedance in a range of about 500 ohms to about 2000 ohms, for example. In such instances, the second range of impedance can be selected from a range of about 500 ohms to about 2000 ohms. In at least on example, the second range of impedance can be about 500 ohms to about 1000 ohms. In at least on example, the second range of impedance can be about 1000 ohms to about 2000 ohms. In at least on example, the second range of impedance can be about 500 ohms to about 1500 ohms. Other values for the second range of impedance are contemplated by the present disclosure.

In certain instances, the semi-conductive spacer 50 may comprise an impedance (Z1). In such instances, in at least one example, the second range of impedance can be the impedance (Z1) ±1% of the impedance (Z1). In another example, the second range of impedance can be the impedance (Z1) ±5% of the impedance (Z1). In yet another example, the second range of impedance can be the impedance (Z1) ±10% of the impedance (Z1). In yet another example, the second range of impedance can be the impedance (Z1) ±50% of the impedance (Z1).

In one embodiment, the present disclosure provides a circuit 1000 configured to implement the logic diagram of FIG. 9 and/or variations thereof. In certain instances, the circuit 1000 can be configured to determine whether an end effector 10 is in the open configuration, the approximated configuration, or the fully approximated configuration. In addition, the circuit 1000 can be configured to generate an appropriate response based on the outcome of the determination. As described above, whether energy is transmitted between the electrodes 92, 94, in response to activation of the energy switch 18, can indicate the configuration of the end effector 10. In one example, an energy transmission between the electrodes 92, 94 is assessed by measuring an impedance (Z) between the electrodes 92, 94. Alternatively, current and/or voltage can be measured instead to assess the energy transmission between the electrodes 92, 94. In any event, the circuit 1000 may be configured to detect activation of the energy switch 18, measure an impedance (Z) between the electrodes 92, 94, and generate the first response when the measured impedance (Z) is greater than or equal to the threshold impedance (Zt), generate the second response when the measured impedance (Z) is in the first range of impedance, or generate the third response when the measured impedance (Z) is in the second range of impedance different from the first range of impedance.

In certain instances, the logic diagram of the present disclosure such as, for example, the logic diagram of FIG. 9 may be implemented by one or more hardware components, one or more software components, or combinations of hardware and software components. In certain instances, the hardware components may include electrical and/or electronic circuits. Such circuits may comprise processors, microprocessors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In certain instances, the software component may include machine executable instructions commonly referred to as programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether to employ hardware components and/or software components to implement the logic diagram of the present disclosure may vary in accordance with any number of factors, such as desired computational rate, power levels, heat tolerances, processing cycle budget, input data rates, output data rates, memory resources, data bus speeds and other design or performance constraints.

In certain instances, the logic diagram of the present disclosure such as, for example, the logic diagram of FIG. 9 may be implemented, for example, by logic (e.g., instructions, data, and/or code) to be executed by a logic device (e.g., processor). Such logic may be stored internally or externally to a logic device on one or more types of computer-readable storage media and/or memory (e.g., flash memory).

Figure 10:
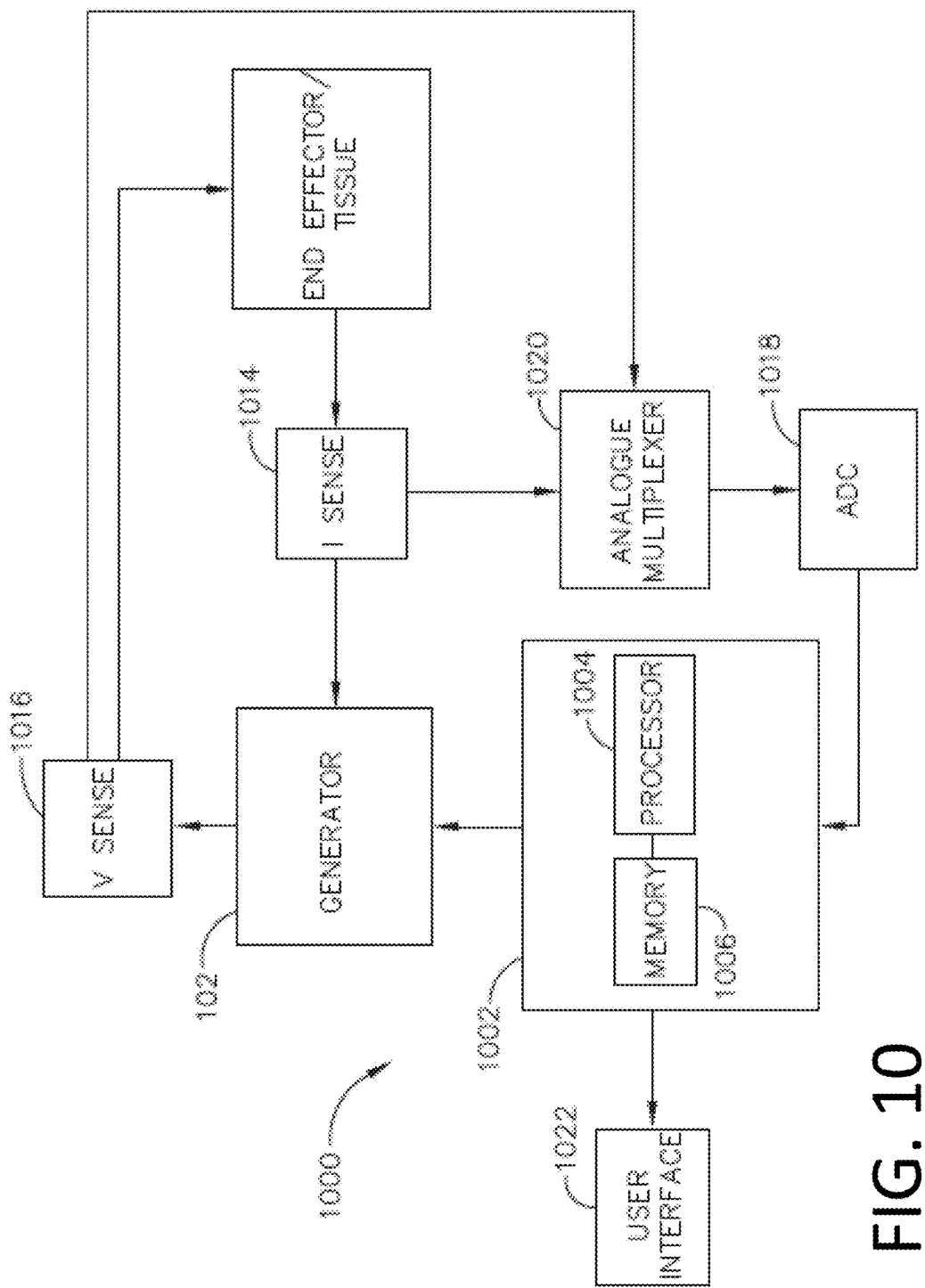
FIG. 10 illustrates a circuit for implementing the logic diagram of FIG. 9, according to one embodiment.

In one embodiment, as illustrated in FIG. 10, the circuit 1000 may comprise a controller 1002. The controller 1002 may comprise one or more processors 1004 (e.g., microprocessor, microcontroller) coupled to at least one memory circuit 1006. The at least one memory circuit 1006 stores machine executable instructions that when executed by the processor 1004, cause the processor 1004 to detect activation of the energy switch 18, measure an impedance (Z) between the electrodes 92, 94, and generate the first response when the measured impedance (Z) is greater than or equal to the threshold impedance (Zt), generate the second response when the measured impedance (Z) is in the first range of impedance, or generate the third response when the measured impedance (Z) is in the second range of impedance different from the first range of impedance.

Figure 11:
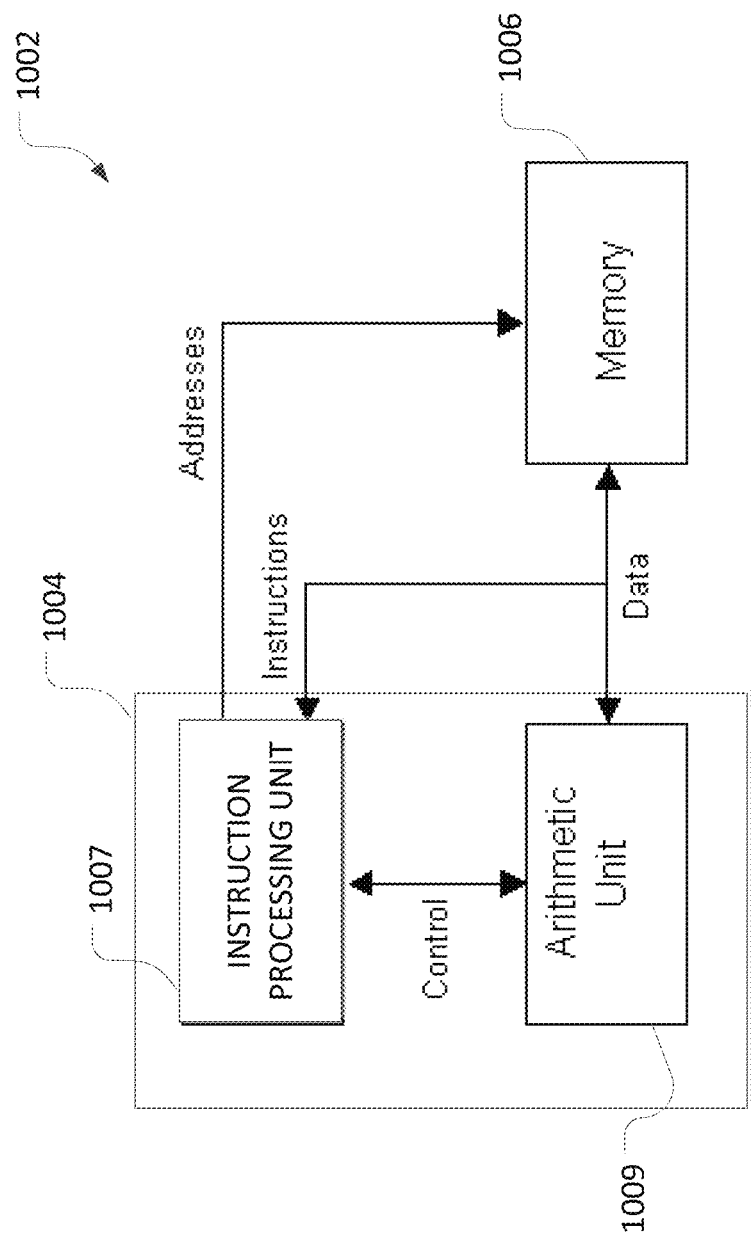
FIG. 11 illustrates a controller for use with the circuit of FIG. 10, according to one embodiment.

The processor 1004 may be any one of a number of single or multi-core processors known in the art. The memory circuit 1006 may comprise volatile and non-volatile storage media. In one embodiment, as illustrated in FIG. 11, the processor 1004 may include an instruction processing unit 1007 and an arithmetic unit 1009. The instruction processing unit may be configured to receive instructions from the one memory circuit 1006.

In certain instances, as illustrated in FIG. 10, a current sense circuit 1014 can be employed to sense current flowing between the electrodes 92, 94. Furthermore, a voltage sense circuit 1016 can be employed to sense an output voltage applied to the electrodes 92, 94 by an energy source such as, for example a generator 102. The sensed values of current and voltage may be applied to an analog-to-digital converter (ADC) 1018 via an analog multiplexer 1020 circuit or switching circuit arrangement. The analog multiplexer 1020 may transmit the appropriate samples of the analog signal to the ADC 1018 for conversion. The processor 1004 may be configured to receive the digital output of the ADC 1018 and calculate the impedance (Z) based on the measured values of current and voltage, for example. Other techniques for determining the impedance (Z) are contemplated by the present disclosure.

In certain instances, one or more of the switches described by the present disclosure such as, for example, the energy switch 18 may comprise mechanical switches, electro-mechanical switches, and/or solid state switches. In certain instances, one or more of the switches of the present disclosure such as, for example, the energy switch 18 may comprise open, inactive, and/or non-conductive positions, states, and/or configurations. In certain instances, one or more of the switches of the present disclosure such as, for example, the energy switch 18 may comprise closed, active, and/or conductive positions, states and/or configurations. In certain instances, one or more of the switches of the present disclosure such as, for example, the energy switch 18 can be transitioned from the open, inactive, and/or non-conductive positions, states, and/or configurations to the closed, active, and/or conductive positions, states and/or configurations to close and/or activate one or more circuits associated with such switches, for example.

In one embodiment, the energy switch 18 can be associated with an activation circuit (not shown) which can be operably coupled to the controller 1002. The activation circuit of the energy switch 18 may be transitioned from an open configuration to a closed configuration in response to activation of the energy switch 18. The processor 1004 can be configured to detect the transition of the activation circuit to the closed configuration. The transition of the activation circuit to the closed configuration may indicate to the processor 1004 that the energy switch 18 is activated. The processor 1004 can be configured to measure the impedance (Z), as described above, in response to the transition of the activation circuit to the closed configuration.

In certain instances, the selected values of the threshold impedance (Zt), the first range of impedance, and/or the second range of impedance can be stored in at least one memory circuit such as, for example, the at least one memory circuit 1006. The processor 1004 may be configured to compare the measured value of the impedance (z) to the stored values of the threshold impedance (Zt), the first range of impedance, and/or the second range of impedance stored in the at least one memory circuit 1006. When the measured impedance (Z) is greater than or equal to the threshold impedance (Zt), the processor 1004 may generate the first response; when the measured impedance (Z) is in the first range of impedance, the processor 1004 may generate the second response; and when the measured impedance (Z) is in the second range of impedance, the processor 1004 may generate the third response.

In certain instances, the parameters of the first response, the second response, and/or the third response are stored in at least one memory circuit such as, for example, the at least one memory circuit 1006. The processor 1004 may employ a user interface 1022 to generate the first response, the second response, and/or the third response, for example. In certain instances, the user interface 1022 may comprise visual feedback devices (e.g., an LCD display screen, LED indicators), audio feedback devices (e.g., a speaker, a buzzer) and/or tactile feedback devices (e.g., haptic actuators), for example.

Figure 12:
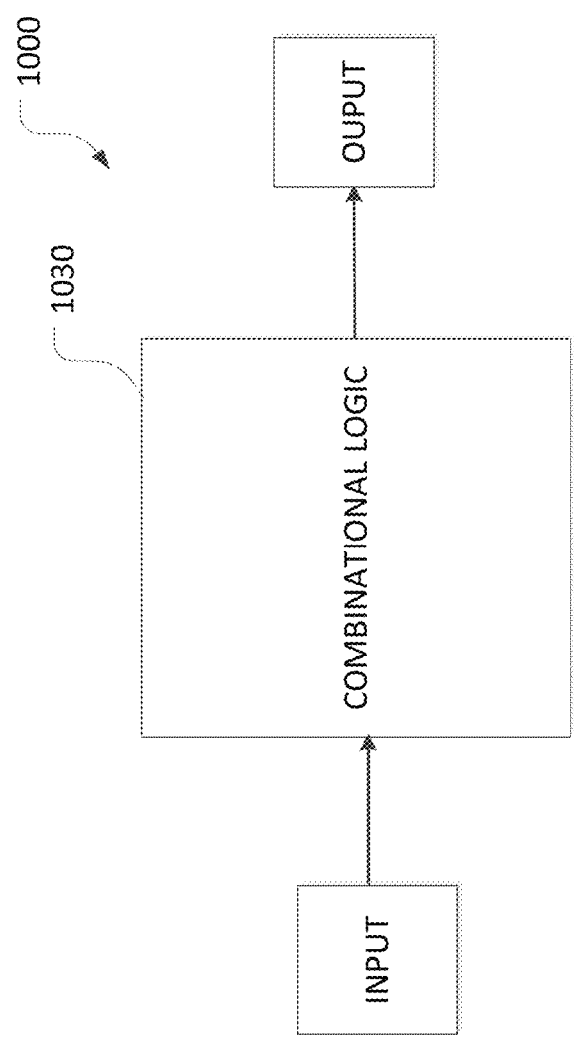
FIG. 12 illustrates a combinational logic circuit for use with the circuit of FIG. 10, according to one embodiment.
Figure 13:
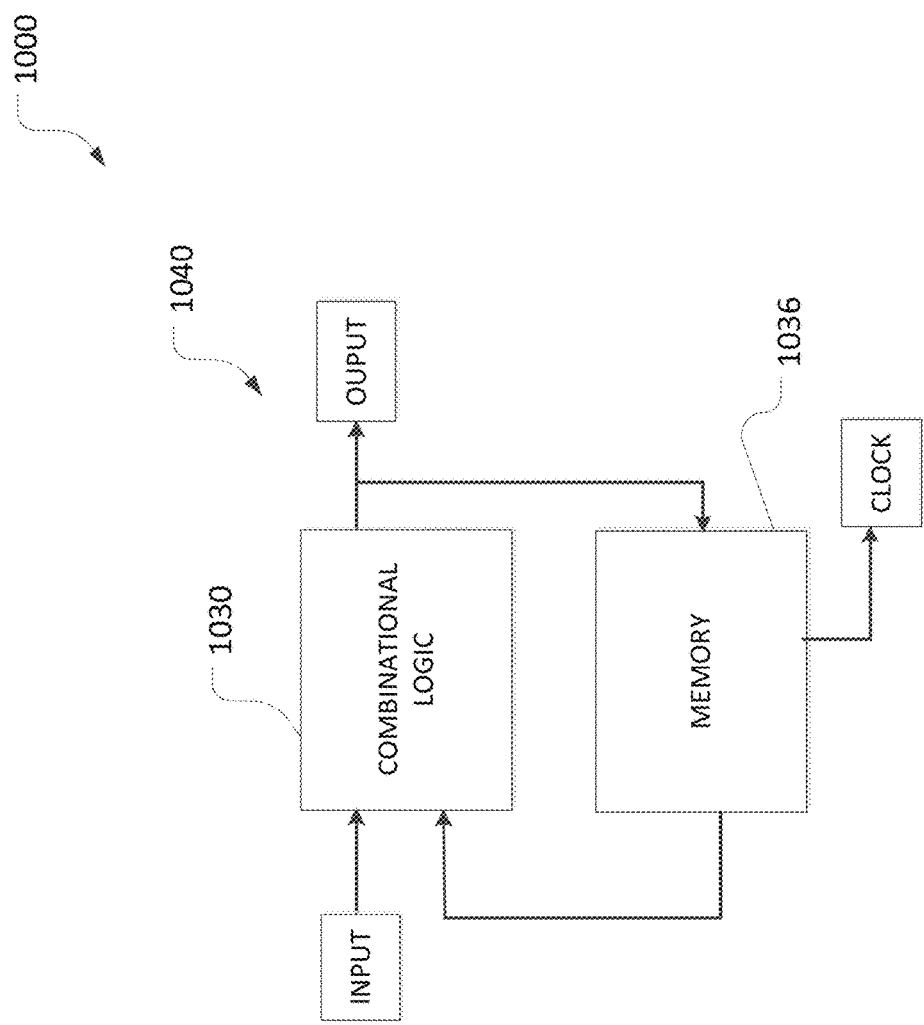
FIG. 13 illustrates a sequential logic circuit for use with the circuit of FIG. 10, according to one embodiment.

In one embodiment, the circuit 1000 may comprise a finite state machine comprising a combinational logic circuit 1030, as illustrated in FIG. 12. In one embodiment, the circuit 1000 may comprise a finite state machine comprising a sequential logic circuit 1040, as illustrated in FIG. 13. The sequential logic circuit 1040 may comprise the combinational logic circuit 1030 and at least one memory circuit 1036, for example. The at least one memory circuit 1036 can store a current state of the finite state machine, as illustrated in FIG. 13. The sequential logic circuit 1040 or the combinational logic circuit 1030 can be configured to cause the finite state machine to detect activation of the energy switch 18, measure an impedance (Z) between the electrodes 92, 94, and generate the first response when the measured impedance (Z) is greater than or equal to the threshold impedance (Zt), generate the second response when the measured impedance (Z) is in the first range of impedance, or generate the third response when the measured impedance (Z) is in the second range of impedance different from the first range of impedance. In certain instances, the sequential logic circuit 1040 may be synchronous or asynchronous.

In other embodiments, the circuit 1000 may comprise a combination of the processor 1004 and the finite state machine to detect activation of the energy switch 18, measure an impedance (Z) between the electrodes 92, 94, and generate the first response when the measured impedance (Z) is greater than or equal to the threshold impedance (Zt), generate the second response when the measured impedance (Z) is in the first range of impedance, or generate the third response when the measured impedance (Z) is in the second range of impedance different from the first range of impedance. In other embodiments, the finite state machine may comprise a combination of the combinational logic circuit 1030 and the sequential logic circuit 1040.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, and application program interface (API), exchanging messages, and so forth.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the embodiments described herein will be processed before surgery. First, a new or used instrument is obtained and when necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is the to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is the to be incorporated by reference herein, but which conflicts with existing definitions, statements, or other disclosure material set forth herein will only be incorporated to the extent that no conflict arises between that incorporated material and the existing disclosure material.

While the present disclosure provides example designs, the claimed subject matter may be further modified within the scope of the disclosure. This application is therefore intended to cover any variations, uses, or adaptations of the present disclosure using its general principles. Further, this application is intended to cover such departures from the present disclosure as come within known or customary practice in the art to which this invention pertains.

The entire disclosures of:

U.S. patent application Ser. No. 14/563,091, entitled ELECTRODE CONFIGURATIONS FOR SURGICAL INSTRUMENTS, filed Dec. 8, 2014;

U.S. patent application Ser. No. 12/576,789, entitled SURGICAL INSTRUMENT FOR TRANSMITTING ENERGY TO TISSUE COMPRISING NON-CONDUCTIVE GRASPING PORTIONS, filed Oct. 9, 2009, now U.S. Pat. No. 8,747,404;

U.S. patent application Ser. No. 14/075,839, entitled ELECTROSURGICAL DEVICES, filed Nov. 8, 2013;

U.S. patent application Ser. No. 14/075,863, entitled ELECTROSURGICAL DEVICES, filed Nov. 8, 2013; and U.S. patent application Ser. No. 14/229,033, entitled DISTAL SEALING END EFFECTOR WITH SPACERS, filed Mar. 28, 2014, are hereby incorporated by reference herein.

What is claimed is:

1. A surgical instrument, comprising:
an end effector, comprising:
a first jaw comprising a first electrode;
a second jaw, wherein at least one of the first jaw and the second jaw is movable relative to the other one of the first jaw and the second jaw to transition the end effector between an open configuration, an approximated configuration, and a fully approximated configuration, and wherein the second jaw comprises:
a second electrode, wherein tissue is captured between the first electrode and the second electrode in the approximated configuration; and
at least one spacer extending from the second electrode, wherein the at least one spacer is configured to maintain a minimum predetermined distance between the first electrode and the second electrode when the end effector is in the fully approximated configuration, and wherein the at least one spacer is simultaneously in contact with the first electrode and the second electrode in the fully approximated configuration;
a switch configured to control energy transmission between the first electrode and the second electrode, wherein the switch is activatable to permit energy transmission between the first electrode and the second electrode; and
a circuit configured to:
detect activation of the switch;
detect an impedance between the first electrode and the second electrode in response to the activation of the switch;
generate a first response corresponding to the open configuration of the end effector when the impedance is greater than or equal to a predetermined threshold;

generate a second response corresponding to the approximated configuration of the end effector when the impedance is in a first range of impedance; and generate a third response corresponding to the fully approximated configuration when the impedance is in a second range of impedance different from the first range of impedance.

2. The surgical instrument of claim 1, wherein the second range of impedance is defined by an impedance of the at least one spacer.

3. The surgical instrument of claim 1, wherein the at least one spacer comprises a semi-conductive material.

4. The surgical instrument of claim 1, wherein the second range of impedance is selected from a range of about 500 ohms to about 2000 ohms.

5. The surgical instrument of claim 1, wherein the first range of impedance is defined by an impedance of the tissue.

6. The surgical instrument of claim 1, wherein the first range of impedance is selected from a range of about 3 ohms to about 400 ohms.

7. The surgical instrument of claim 1, wherein the circuit comprises a finite state machine configured to:
    detect the activation of the switch;
    detect the impedance between the first electrode and the second electrode in response to the activation of the switch;
    generate the first response corresponding to the open configuration of the end effector when the impedance is greater than or equal to the predetermined threshold;
    generate the second response corresponding to the approximated configuration of the end effector when the impedance is in the first range of impedance; and
    generate the third response corresponding to the fully approximated configuration when the impedance is in the second range of impedance.

8. The surgical instrument of claim 1, wherein the circuit comprises:
    a processor; and
    a memory that stores program instructions, which when executed from the memory cause the processor to:
        detect the activation of the switch;
        detect the impedance between the first electrode and the second electrode in response to the activation of the switch;
        generate the first response corresponding to the open configuration of the end effector when the impedance is greater than or equal to the predetermined threshold;
        generate the second response corresponding to the approximated configuration of the end effector when the impedance is in the first range of impedance; and
        generate the third response corresponding to the fully approximated configuration when the impedance is in the second range of impedance.

9. The surgical instrument of claim 8, wherein the circuit comprises a finite state machine, wherein the finite state machine comprises at least one combinational logic circuit configured to cause the finite state machine to:
    detect the activation of the switch;
    detect the impedance between the first electrode and the second electrode in response to the activation of the switch;
    generate the first response corresponding to the open configuration of the end effector when the impedance is greater than or equal to the predetermined threshold;
    generate the second response corresponding to the approximated configuration of the end effector when the impedance is in the first range of impedance; and
    generate the third response corresponding to the fully approximated configuration when the impedance is in the second range of impedance.

10. The surgical instrument of claim 8, wherein the circuit comprises a finite state machine, wherein the finite state machine comprises at least one sequential logic circuit coupled to at least one memory circuit, the at least one memory circuit configured to store a current state of the finite state machine, wherein the sequential logic circuit is configured to cause the finite state machine to:
    detect the activation of the switch;
    detect the impedance between the first electrode and the second electrode in response to the activation of the switch;
    generate the first response corresponding to the open configuration of the end effector when the impedance is greater than or equal to the predetermined threshold;
    generate the second response corresponding to the approximated configuration of the end effector when the impedance is in the first range of impedance; and
    generate the third response corresponding to the fully approximated configuration when the impedance is in the second range of impedance.

11. The surgical instrument of claim 10, wherein the sequential logic circuit is either synchronous or asynchronous.

* * * * *